(12) United States Patent
Nguyen et al.

(10) Patent No.: US 8,629,094 B2
(45) Date of Patent: Jan. 14, 2014

(54) ODOR ELIMINATION COMPOSITION FOR USE ON SOFT SURFACES

(75) Inventors: Peter N. Nguyen, Racine, WI (US);
Cary E. Manderfield, Racine, WI (US);
Maciej K. Tasz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 13/208,990

(22) Filed: Aug. 12, 2011

(65) Prior Publication Data

US 2012/0027713 A1 Feb. 2, 2012

Related U.S. Application Data

(63) Continuation of application No. 11/759,766, filed on Jun. 7, 2007, now Pat. No. 8,022,026, which is a continuation-in-part of application No. 11/313,297, filed on Dec. 20, 2005, now Pat. No. 7,262,159.

(51) Int. Cl.
*C11D 1/835* (2006.01)
*C11D 3/44* (2006.01)

(52) U.S. Cl.
USPC .......... 510/287; 510/289; 510/293; 510/295; 510/308; 510/329; 510/330; 510/341; 510/342; 510/356; 510/384; 510/421; 510/432; 510/504; 510/515; 510/524; 510/525

(58) Field of Classification Search
USPC ......... 510/287, 289, 293, 295, 308, 329, 330, 510/341, 342, 356, 384, 421, 432, 504, 515, 510/524, 525
See application file for complete search history.

(56) References Cited

U.S. PATENT DOCUMENTS

| | | |
|---|---|---|
| 3,160,555 A | 12/1964 | Hamill et al. |
| 3,567,118 A | 3/1971 | Shepherd et al. |
| 3,943,242 A | 3/1976 | Fogel et al. |
| 3,993,250 A | 11/1976 | Shure |
| 4,048,369 A | 9/1977 | Johnson |
| 4,078,055 A | 3/1978 | Naganuma et al. |
| 4,184,985 A | 1/1980 | Scheuermann et al. |
| 4,202,800 A | 5/1980 | Ciko et al. |
| 4,275,054 A | 6/1981 | Sebag et al. |
| 4,294,821 A | 10/1981 | Neumiller |
| 4,304,679 A | 12/1981 | Hooper et al. |
| 4,511,486 A | 4/1985 | Shah |
| 4,540,721 A | 9/1985 | Staller |
| 4,606,842 A | 8/1986 | Keyes et al. |
| 4,652,389 A | 3/1987 | Moll |
| 4,690,779 A | 9/1987 | Baker et al. |
| 4,816,220 A | 3/1989 | Roychowdhury |
| 4,880,557 A | 11/1989 | Ohara et al. |
| 4,883,651 A | 11/1989 | Meyer |
| 4,906,462 A | 3/1990 | Miki et al. |
| 4,934,609 A | 6/1990 | Lindauer et al. |
| 4,938,416 A | 7/1990 | Bertrand et al. |
| 5,094,761 A | 3/1992 | Trinh et al. |
| 5,102,564 A | 4/1992 | Gardlik et al. |
| 5,126,068 A | 6/1992 | Burke et al. |
| 5,219,890 A | 6/1993 | Boucher |
| 5,380,707 A | 1/1995 | Barr et al. |
| 5,444,094 A | 8/1995 | Malik et al. |
| 5,578,563 A | 11/1996 | Trinh et al. |
| 5,593,670 A | 1/1997 | Trinh et al. |
| 5,663,134 A | 9/1997 | Trinh et al. |
| 5,668,097 A | 9/1997 | Trinh et al. |
| 5,670,475 A | 9/1997 | Trinh et al. |
| 5,714,137 A | 2/1998 | Trinh et al. |
| 5,783,544 A | 7/1998 | Trinh et al. |
| 5,939,060 A | 8/1999 | Trinh et al. |
| 5,942,217 A | 8/1999 | Woo et al. |
| 5,955,093 A | 9/1999 | Woo et al. |
| 5,955,414 A | 9/1999 | Brown et al. |
| 5,968,404 A | 10/1999 | Trinh et al. |
| 5,997,759 A | 12/1999 | Trinh et al. |
| 6,001,343 A | 12/1999 | Trinh et al. |
| 6,033,679 A | 3/2000 | Woo et al. |
| 6,034,261 A | 3/2000 | Matsunaga et al. |
| 6,077,318 A | 6/2000 | Trinh et al. |
| 6,080,387 A | 6/2000 | Zhou et al. |
| 6,106,738 A | 8/2000 | Woo et al. |

(Continued)

FOREIGN PATENT DOCUMENTS

| | | |
|---|---|---|
| DE | 19937871 A1 | 2/2001 |
| FR | 2622204 A | 4/1989 |
| WO | WO 00/54585 A | 9/2000 |
| WO | WO 01/12145 A | 2/2001 |
| WO | WO 01/24835 A | 4/2001 |
| WO | WO 01/37658 A | 5/2001 |
| WO | WO2006/023858 A1 | 3/2006 |
| WO | WO 2007/014152 A | 2/2007 |
| WO | WO 2007/075821 A | 7/2007 |

OTHER PUBLICATIONS

International Search Report and Written Opinion for PCT/US2006/048660 dated Sep. 5, 2007.

International Search Report and Written Opinion for PCT/US2008/007097 dated Nov. 17, 2008.

*Primary Examiner* — Charles Boyer

(57) ABSTRACT

A method and composition for deodorizing soft surfaces such as carpeting and upholstery are disclosed. The method includes the spraying of a liquid composition on a soft surface and allowing the composition to absorb into the soft surface, form liquid agglomerations within the soft surface to the agglomerations can make contact with malodorants disposed within the soft surface. The composition is capable of penetrating rapidly and deeply into the soft surfaces for contacting odor-causing substances embedded therein. The composition comprises an active ingredient such as a glycol or triethanolamine. Other ingredients that contribute to the surface penetration and/or agglomeration formation include ethanol, water, fragrance and a combination of at least one nonionic and at least one ionic surfactant.

16 Claims, 2 Drawing Sheets

(56) References Cited

U.S. PATENT DOCUMENTS

| | | | |
|---|---|---|---|
| 6,146,621 A | 11/2000 | Trinh et al. | |
| 6,177,070 B1 | 1/2001 | Lynch | |
| 6,197,070 B1 | 3/2001 | Horner et al. | |
| 6,248,135 B1 | 6/2001 | Trinh et al. | |
| 6,284,231 B1 | 9/2001 | Trinh et al. | |
| 6,287,346 B1 | 9/2001 | Ofosu-Asante et al. | |
| 6,287,545 B1 * | 9/2001 | Su | 424/70.12 |
| 6,315,949 B1 | 11/2001 | Carmello et al. | |
| 6,395,236 B1 | 5/2002 | Stewart | |
| 6,451,065 B2 | 9/2002 | Trinh et al. | |
| 6,454,876 B1 | 9/2002 | Ochomogo et al. | |
| 6,471,974 B1 | 10/2002 | Rees et al. | |
| 6,482,392 B1 | 11/2002 | Zhou et al. | |
| 6,528,472 B2 | 3/2003 | Charaf et al. | |
| 6,573,233 B1 | 6/2003 | Almann et al. | |
| 6,680,289 B1 * | 1/2004 | Woo et al. | 510/470 |
| 6,767,507 B1 | 7/2004 | Woo et al. | |
| 6,780,403 B1 | 8/2004 | Yamashita et al. | |
| 6,794,346 B2 | 9/2004 | Wick et al. | |
| 6,814,088 B2 | 11/2004 | Barnabas et al. | |
| 6,867,174 B2 | 3/2005 | Ramirez, Jr. et al. | |
| 6,943,140 B2 | 9/2005 | Ashton et al. | |
| 7,082,951 B2 | 8/2006 | Barnabas et al. | |
| 7,094,741 B2 | 8/2006 | Barnabas et al. | |
| 2002/0011584 A1 | 1/2002 | Uchiyama et al. | |
| 2002/0039566 A1 | 4/2002 | Triplett et al. | |
| 2002/0132861 A1 | 9/2002 | Uchiyama et al. | |
| 2003/0027737 A1 | 2/2003 | Evers | |
| 2003/0044309 A1 | 3/2003 | Hernandez et al. | |
| 2003/0045439 A1 | 3/2003 | Evers | |
| 2003/0145965 A1 | 8/2003 | Anderson et al. | |
| 2003/0162678 A1 | 8/2003 | Ashton et al. | |
| 2003/0191034 A1 | 10/2003 | Woo et al. | |
| 2003/0199402 A1 | 10/2003 | Triplett et al. | |
| 2003/0216488 A1 * | 11/2003 | Uchiyama et al. | 523/102 |
| 2004/0147416 A1 | 7/2004 | Woo et al. | |
| 2004/0213750 A1 | 10/2004 | Bennett et al. | |
| 2005/0003990 A1 | 1/2005 | Smith et al. | |
| 2005/0060811 A1 | 3/2005 | Smith et al. | |
| 2005/0089540 A1 | 4/2005 | Uchiyama et al. | |
| 2005/0100520 A1 | 5/2005 | Hagura et al. | |
| 2005/0166938 A1 * | 8/2005 | Hoepfl et al. | 132/200 |
| 2005/0196374 A1 | 9/2005 | Ueda | |
| 2005/0202991 A1 | 9/2005 | De Dominicis et al. | |
| 2005/0227897 A1 | 10/2005 | Nelson et al. | |
| 2006/0228250 A1 | 10/2006 | Brown et al. | |
| 2006/0258768 A1 | 11/2006 | Uchiyama et al. | |
| 2006/0288516 A1 | 12/2006 | Sawalski | |
| 2007/0021316 A1 | 1/2007 | Dilley et al. | |
| 2007/0050915 A1 | 3/2007 | Frankenbach | |
| 2007/0072785 A1 | 3/2007 | Sahin Topkara et al. | |
| 2008/0021098 A1 | 1/2008 | McGee et al. | |
| 2008/0293811 A1 * | 11/2008 | Oguchi et al. | 514/547 |

* cited by examiner

ODOR ELIMINATION COMPOSITION FOR USE ON SOFT SURFACES

CROSS-REFERENCE TO RELATED APPLICATION

This application is a continuation of application Ser. No. 11/759,766, filed on Jun. 7, 2007, which is a continuation-in-part of application Ser. No. 11/313,297, filed on Dec. 20, 2005.

BACKGROUND

1. Technical Field

An improved odor elimination composition is disclosed which effectively removes odors embedded in soft surfaces such as carpeting and upholstery. The improved composition makes use of triethylene glycol and a combination of non-ionic and ionic surfactants, one of which has bactericidal properties. The improved composition rapidly penetrates deep into the soft surfaces for providing fast and effective odor elimination. Methods for evaluating the ability of the composition to penetrate soft surfaces are also disclosed.

2. Description of the Related Art

It has been known to use certain glycols in aerosol or vapor forms to sanitize air in a room by killing airborne bacteria. One particular glycol, triethylene glycol ("TEG"), has been found particularly effective for sanitizing air when delivered via an aerosol spray. The commercially successful OUST® air sanitizer products utilize a mixture that contains about 6 wt % TEG. Non-aerosol applications of TEG for disinfecting air are also developed.

The structure of triethylene glycol is illustrated below:

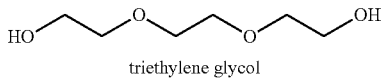

triethylene glycol

TEG is a colorless, odorless, non-volatile and hygroscopic liquid. It is characterized by two hydroxyl groups along with two ether linkages which contribute to its high water solubility, hygroscopicity and its ability to neutralize airborne odor-causing bacteria. TEG can be prepared commercially by the oxidation of ethylene at high temperatures in the presence of a silver oxide catalyst, following by hydration of the ethylene oxide to yield mono-, di-, tri- and tetra-ethylene glycol products. TEG has low toxicity.

Until now, the treatment and removal of odor-causing substances from soft surfaces such as clothing, drapes, bedding, carpeting and upholstery utilize very different mechanisms. One strategy uses aqueous formulations containing water-soluble cyclodextrins for odor control or odor elimination. These formulations also use water-soluble metallic salts in addition to the water-soluble cyclodextrins.

Cyclodextrins have a toroidal structure, the interior of which is hydrophobic. The exterior of this toroid structure is hydrophilic thereby rendering them water-soluble. It has been found that hydrophobic odor-causing substance enters the hydrophobic interior of a cyclodextrin toroid and forms a stable complex with the cyclodextrin structure due to the interplay of Van der Waals forces, the effects of hydrogen bonding and the common hydrophobicity of the cyclodextrin interior and odor-causing substance.

By forming stable complexes with odor-causing substance, cyclodextrins keep the substances out of the air thereby reducing the odor caused thereby. Water-soluble metallic salts may be combined with the cyclodextrins to absorb amines and sulfur-containing compounds.

A second strategy utilizes formulations that include water soluble/dispersible polymers for containing and controlling odor-causing substance. In contrast to cyclodextrins, which entrap or cage the odor-causing substance within the cyclodextrin toroid as discussed above, the water soluble/dispersible polymer entraps the odor-causing substance by forming a film that blankets the odor-causing substance.

The film is formed as the solvent or carrier of the formulation evaporates. Thus, the residual polymer film provides a barrier for containing the odor-causing substance within the soft surface thereby preventing it from being released to the ambient environment and detected by a consumer's sense of smell.

As both the cyclodextrins and film-forming polymers are large molecules that are difficult to evaporate, the above discussed formulations leave a visible residue after the solvent or carrier of the formulations evaporates. Further, neither cyclodextrins nor film-forming polymers have any anti-microbial properties.

Another problem associated with known odor-elimination formulations is the lack of ability to penetrate rapidly and deeply into the soft surfaces and eliminate odor-causing substance trapped (or embedded) therein. As a result, although temporary odor elimination can be achieved by using the known formulations, recurrence of odors usually happens when deeply embedded odor-causing substance relocates or "rises" from its original location. In such cases, reapplication of the formulations is generally needed at relatively short intervals.

Other more drastic measures for treating odor-causing substance trapped in carpeting, upholstery and clothing involve the use of enzymes or detergents to remove the odor-causing substance. In the case of upholstery and carpeting, professional services or the renting of special machinery is often required.

Therefore, there is a need for an improved method for removing odors in soft surfaces that are not easily washable, i.e., carpeting and upholstery. Moreover, there is a need for an improved odor elimination composition that may be sprayed onto carpeting or upholstery; that will not discolor or form a film or residue on the carpeting or upholstery; and that will penetrate rapidly and deeply into the soft surfaces to effectively deliver active odor-neutralizing ingredients to odor-causing substance embedded therein.

SUMMARY OF THE DISCLOSURE

In satisfaction of the afore noted needs, a method and a composition are disclosed for eliminating odors deeply embedded in soft surfaces such as carpeting, upholstery, clothing, bed linens, etc.

In an embodiment, a disclosed method for deodorizing soft surfaces comprises spraying a composition on a soft surface, wherein the composition comprises an active ingredient that is a liquid at room temperature and has a vapor pressure at room temperature of less than 0.0035 mmHg, and allowing the formulation to rapidly penetrate deep into the soft surface and make contact with an odor-causing substance trapped therein.

The active ingredient that is a liquid at room temperature and that has a vapor pressure at room temperature of less than 0.0035 mmHg at room temperature may be one or more glycols and other suitable materials that eliminates, counteracts, and/or neutralizes the odor-causing substances. Substances suitable for use as the active ingredient will be apparent to those of ordinary skill in the art and should be considered within the scope of this disclosure.

In a refinement, the active ingredient is a glycol selected from the group consisting of triethylene glycol (TEG), dipropylene glycol, propylene glycol and combinations thereof. Triethanolamine is also a suitable active ingredient.

In an embodiment, a disclosed method for deodorizing soft surfaces comprises spraying a liquid composition on a soft surface wherein the liquid composition comprises an active ingredient that may be a glycol selected from the group consisting of triethylene glycol (TEG), dipropylene glycol, and propylene glycol or other ingredients having a vapor pressure at room temperature of less than 0.0035 mmHg, and allowing the composition to penetrate deep into the soft surface and make contact with an odor-causing substance trapped therein.

In such a method, agglomerations of the active ingredient, carrier, fragrance and surfactant form and rapidly penetrate deep into the soft surfaces. When odor-causing substance trapped therein engages these agglomerations, the odor-causing substance is dissolved into, or absorbed by, the agglomeration thereby reducing the partial vapor pressure of the odor-causing substance and the odor caused thereby. As the glycol or other active ingredient remains in a liquid form, no dried residue is apparent or visible.

In a refinement, the disclosed composition further comprises water and a low molecular weight alcohol such as a short chain monohydric alcohol. In a further refinement of this concept, the alcohol is selected from the group consisting of ethanol, isopropanol, butanol and propanol. Ethanol is currently preferred due to its low cost and acceptable odor. Additional co-solvents include glycol ethers such as glycol monoethyl ether and diethylene glycol butyl ether.

The alcohol and water both act as solvents or carriers and the alcohol reduces the drying time of the disclosed liquid composition. Preferably, the alcohol is a minor component compared to that of water, with the water content ranging from about 75-95 wt % and the alcohol content ranging from about 1 to about 10 wt %, most preferably about 6 wt %.

In another refinement, the disclosed composition further comprises a plurality of surfactants. The surfactants may comprise a plurality of nonionic surfactants, a combination of nonionic and ionic surfactants, or, more specifically, a combination of nonionic and cationic surfactants. Amphoteric and zwitterionic surfactants may also be used.

In a further refinement of this concept, the plurality of surfactants includes at least one ionic surfactant and at least one nonionic surfactant. The surfactants used in the composition may also be known in others applications as emulsifiers and, for the purposes of this disclosure, the terms surfactant and emulsifier will be considered to be interchangeable as the common property of surfactants and emulsifiers, i.e., reducing surface tension, is the important function for purposes of this application. Combinations of nonionic surfactants have been found to be effective as well as combinations of nonionic and cationic surfactants.

In a refinement, the nonionic surfactant comprises a combination of an ether and a hydrogenated oil. In a further refinement, the nonionic surfactants comprise a combination of polyglycol ether and a hydrogenated castor oil. In still a further refinement, polyglycol ether is a polyoxyethylene alkylether.

In another refinement, the ionic surfactant is a cationic surfactant. Preferably, the cationic surfactant comprises a quaternary ammonium salt. One benefit of using the quaternary ammonium salt is its anti-bacterial properties of these salts.

One disclosed composition for carrying out the above-described method comprises: water; a short chain monohydric alcohol; a glycol selected from the group consisting of triethylene glycol (TEG), dipropylene glycol, propylene glycol, and combinations thereof or another material that is a liquid at room temperature and that has a vapor pressure at room temperature of less than 0.0035 mmHg at room temperature; fragrance; at least one nonionic surfactant, and at least one ionic surfactant. As noted above, dipropylene glycol and propylene glycol may be substituted for the currently preferred glycol, TEG. Also, as indicated, combinations of these glycols may be used.

In a refinement, the glycol may be present in an amount ranging from 0.5 to about 5 wt %. Most preferably, the glycol, which is preferably but not necessarily TEG, comprises about 1 wt % of the composition.

In another refinement, the disclosed composition comprises from about 1 to about 10 wt % low molecular weight monohydric alcohol or glycol ether, from about 0.5 to about 5 wt % glycol, from about 0.25 to about 0.75 wt % fragrance, from about 1 to about 2 wt % nonionic and ionic surfactants and, the remainder, water. The surfactant content can range from about 0.5 to about 2 wt %.

In a preferred embodiment, the surfactant combination comprises a hydrogenated castor oil, a polyglycol ether, and a quaternary ammonium salt.

In one preferred embodiment, the composition comprises from about 4 to about 8 wt % ethanol, from about 0.5 to about 1.5 wt % TEG, from about 0.5 to about 0.75 wt % fragrance, from about 0.5 to about 1.5 wt % nonionic surfactant, from about 0.1 to about 1 wt % cationic surfactant and, the remainder, water.

In a further refinement of this concept, the nonionic surfactants comprise a combination of a hydrogenated oil and a polyglycol ether. In a further refinement, the ionic surfactant comprises a quaternary ammonium salt. In still a further refinement, the nonionic surfactants may include (1) a hydrogenated castor oil, that includes glycerol and polyethylene glycol oxystearate, and (2) a polyglycol ether that is a ethoxylation product of $C_{11}$ to $C_{15}$ linear secondary alkanols with ethylene oxide.

The disclosed composition preferably penetrates rapidly and deeply into the soft surfaces for contacting the odor-causing substance embedded therein. Methods for evaluating the surface penetration ability of the composition are also provided.

Other advantages and features of the disclosed methods and compositions will be described in greater detail below.

BRIEF DESCRIPTION OF THE DRAWINGS

For a more complete understanding of the disclosed methods and apparatuses, reference should be made to the embodiments illustrated in greater detail in the accompanying drawings, wherein.

Figure 1:
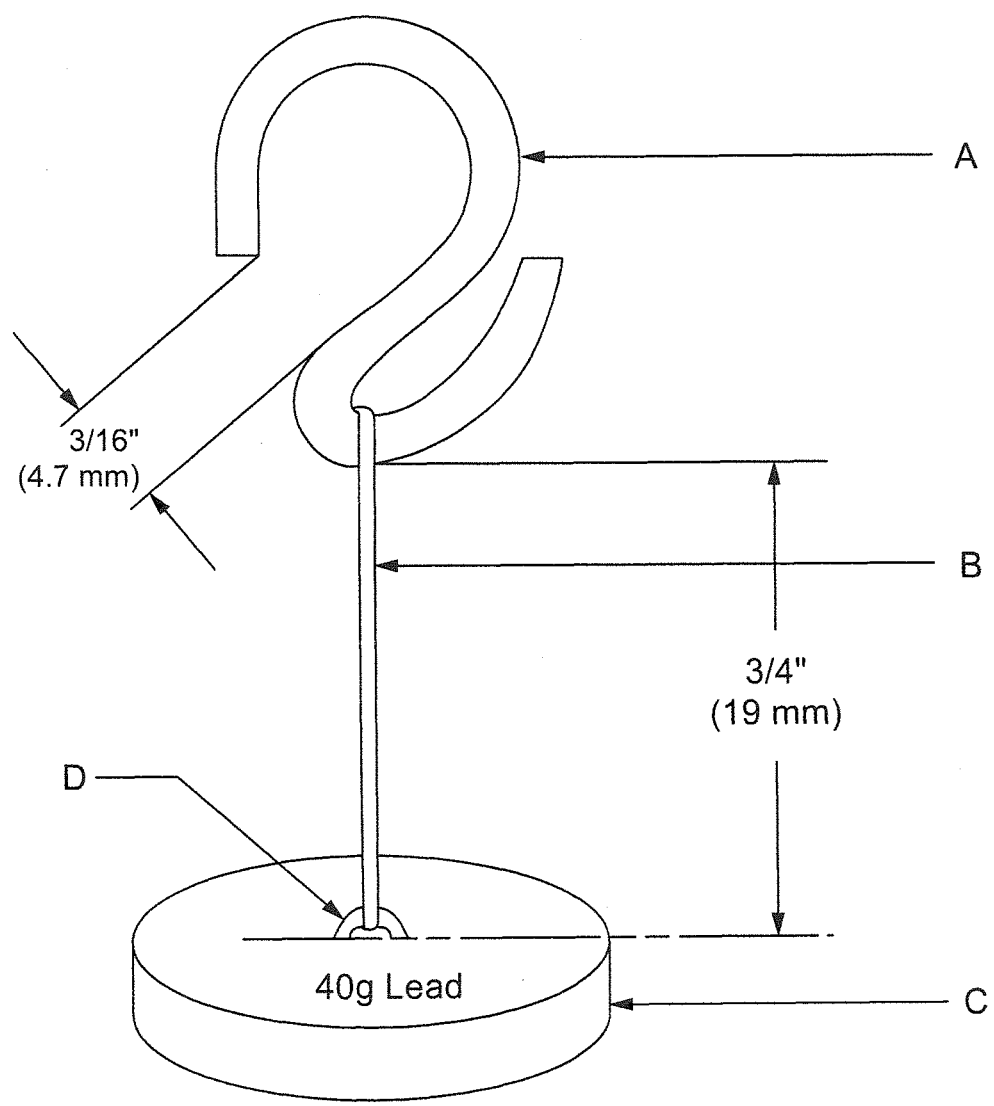
FIG. 1 graphically illustrates the anchoring assembly used in the Skein Test in accordance with this disclosure.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

An improved odor elimination composition for carpeting, upholstery and other soft surfaces is provided. The improved composition delivers an active ingredient to odor-causing substance embedded within soft surfaces thereby enabling active ingredient to come into contact with the odor-causing substance. Without being bound to any particular theory, it is believed that the active ingredient, in combination with other materials of the formulation, form agglomerations within the soft surface. When the odor-causing substance engages these agglomerations, the odor-causing substance is dissolved into the agglomeration thereby reducing the partial vapor pressure of the odor-causing substance to a level below what is needed to be detected by the human sense of smell. As the glycol or other active ingredient remains in a liquid form, the agglomerations remain as liquid agglomerations for an extended period of time and no dried residue is apparent or visible.

Also, when the disclosed compositions are applied to a soft surface, the odor-causing substance adsorbed onto the soft surface are first dissolved in the liquid composition before formation of the agglomerations. As the odor-causing substance desorbs from the soft surface, some of the substance enters the gas phase rather than the composition. The degree to which the odor-causing substance preferentially enters into the gas phase depends on the degree of solubility of the substance in the composition. Molecules with good water solubility will transferred to the applied aqueous phase. Molecules with poor water solubility will desorb from the surface into the air.

Since the agglomeration mechanism for odor elimination is driven by solubility parameters, odor-causing substance having poor water solubility is least likely enter into the aqueous composition and therefore most likely to desorb from the surface into the surrounding air. In order to enhance the solubility of the odor-causing substance in the composition, a mixed solvent system, e.g. water and alcohol or glycol is preferably used. As a result, the disclosed compositions offer a dual action odor elimination mechanism: desorption of malodor from the surface as well as increased solubility of malodor molecules in the applied product. Odors that are desorbed from the surface into the surrounding air can be removed from the home by other means such as natural air change, i.e. ventilation.

After the volatile components of the composition evaporate, the solubilized odor-causing substance remains in the low volatile liquid components, e.g. glycol or TEA, and desorbs at a much slower rate. The degree to which the odor-causing substance enters into the mixed solvent systems can be controlled by adjusting the solubility parameters of the mixed solvent system to more closely match the solubility parameters of the odor-causing substance.

Certain odor-causing substances such as thiols, amines, acids and sulfides readily dissolve into the agglomerations which, by way of an example, can comprise a core portion of the active ingredient (i.e., the glycol or other liquid with a vapor pressure at room temperature of less than 0.0035 mmHg), carrier, fragrance and an outer portion that includes significant amounts of surfactant. Thus, the disclosed formulations do not mask odor-causing compounds and molecules; they keep them from being released by reducing their vapor pressures.

Nine exemplary compositions are disclosed below. It should be noted that this disclosure is not limited to the particular compositions and acceptable ranges of the various ingredients are also set forth below.

Example 1

| Wt % | Name/Formula | Function |
|---|---|---|
| 92.325 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.25 | fragrance oil mixture (TAKASAGO RK-1428, outdoor) | fragrance |
| 0.2650 | PROTACHEM ™ CAH-60, hydrogenated castor oil (glycerol, polyethylene glycol oxystearate) | nonionic surfactant |
| 0.11 | SOFTANOL ™ 70, polyoxyethylene alkylether | nonionic surfactant |
| 100.0000 | | |

Example 2

| Wt % | Name/Formula | Function |
|---|---|---|
| 92.325 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.25 | fragrance oil mixture (TAKASAGO RK-1428, outdoor) | fragrance |
| 0.2650 | PROTACHEM ™ CAH-60, hydrogenated castor oil (glycerol, polyethylene glycol oxystearate) | nonionic surfactant |
| 0.11 | TERGITOL ™ 15-s-7, polyglycol ether | nonionic surfactant |
| 100.00 | | |

Example 3

| Wt % | Name/Formula | Function |
|---|---|---|
| 91.45 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.15 | Agent 2248-14, quaternary ammonium salt | cationic surfactant |
| 100.00 | | |

Example 4

| Wt % | Name/Formula | Function |
|---|---|---|
| 91.2 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

Example 5

| Wt % | Name/Formula | Function |
|---|---|---|
| 91.2 | de-ionized water | solvent/carrier |
| 6.0 | isopropanol, $(CH_3)_2CHOH$ | solvent/carrier |
| 1.00 | TEA, triethanolamine $(HOCH_2CH_2)_3N$ | odor remover |
| 0.40 | fragrance oil mixture (TAKASAGO RK-1428, outdoor) | fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

Example 6

| Wt % | Name/Formula | Function |
|---|---|---|
| 91.2 | de-ionized water | solvent/carrier |
| 6.0 | isopropanol, $(CH_3)_2CHOH$ | solvent/carrier |
| 1.00 | Dipropylene glycol | odor remover |
| 0.40 | fragrance oil mixture (TAKASAGO RK-1428, outdoor) | fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

Example 7

| Wt % | Name/Formula | Function |
|---|---|---|
| 90.6 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.40 | Agent 2248-14, quaternary ammonium salt | cationic surfactant |
| 0.60 | nitrogen | propellant |
| 100 | | |

Example 8

| Wt % | Name/Formula | Function |
|---|---|---|
| 71.2 | de-ionized water | solvent/carrier |
| 6.00 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.40 | Agent 2248-14, quaternary ammonium salt | cationic surfactant |
| 20.00 | hydrocarbon propellant (LPG) | propellant |
| 100.00 | | |

Example 9

| Wt % | Name/Formula | Function |
|---|---|---|
| 91.65 | de-ionized water | solvent/carrier |
| 5.90 | ethanol, $CH_3CH_2OH$ | solvent/carrier |
| 1.00 | TEG (98%), triethylene glycol $HO(CH_2)_2O(CH_2)_2O(CH_2)_2OH$ | odor remover |
| 0.30 | fragrance oil mixture | Fragrance |
| 0.375 | PROTACHEM ™ CH-60, hydrogenated castor oil (glycerol, polyethylene glycol oxystearate) | nonionic surfactant |
| 0.375 | TERGITOL ™ 15-s-7, polyglycol ether | nonionic surfactant |
| 0.40 | STENQUAT1010, didecyl dimethyl ammonium chloride | cationic surfactant |
| 100.00 | | |

Water and ethanol serve as carriers and co-solvents. The inclusion of ethanol, or other short chain monohydric alcohols, provides for a faster dry time for the applied composition. Ethanol is also an excellent carrier and therefore assists in delivering the active ingredient to where it is needed. Additional co-solvents include glycol ethers such as glycol monoethyl ether and diethylene glycol butyl ether. The alcohol or glycol ether co-solvent should be present in the range of from about 1 to about 10 wt %.

Because the TEG is provided in a suitable carrier and because it will not quickly evaporate once it has impregnated a soft surface, the amount of TEG may be relatively low as compared at an aerosol air sanitizing formulation. Typically, an air sanitizing formulation will have about 6 wt % TEG; in this particular application, i.e., soft surfaces, the amount of TEG can be reduced to less than 5 wt %. In the examples above, the TEG comprises 1.0 wt % of the formulations. However, depending on the particular use or particular odors being treated, the TEG content can vary widely and could range from 0.5 wt % to 6.0 wt % or more. Examples 1-4 and 7-8 above, with their 1.0 wt % TEG content, are merely currently preferred embodiments.

TEG is not the only glycol that can be used. Dipropylene glycol (Example 6) and propylene glycol are also suitable. Further, an active ingredient that is a liquid at room temperature and that has a vapor pressure at room temperature of less than 0.0035 mmHg may be utilized.

Another alternative to TEG or another glycol is triethanolamine (TEA). See Example 5. Like TEG, TEA is a liquid at room temperature, has a low vapor pressure at room temperature ($3.6 \times 10^{-6}$ mmHg) and has a non-offensive odor.

The fragrances utilized can be obtained from Takashago International Corp., a Japanese corporation having an office at 4 Volvo Drive, Rockleigh, N.J. 07647 (http://www.takashago.com). Of course, one skilled in the art will know that other suppliers of fragrances exist and this disclosure is not limited to the particular fragrances utilized herein. A preferred fragrance range is from about 0.25 to about 0.75 wt %.

Novel combinations of surfactants/emulsifiers are also utilized. Examples 1 and 2 utilize only nonionic surfactants in the form of hydrogenated castor oils and polyglycol ethers. The hydrogenated castor oils are sold under the tradename PROTACHEM™ CAH-60 or TAGAT™ CH-60 with the INCI/CTFA chemical name "PEG-60 hydrogenated castor oil." PROTACHEM™ CAH-60 can be obtained from Protameen Chemicals, Inc., 375 Minnisik Road, Totowa, N.J. 07511. The hydrogenated castor oil includes glycerol stearate, and if ethoxylated, includes polyethylene glycol oxystearate.

The other nonionic surfactant or emulsifier utilized is either TERGITOL™ 15-S-7, which is a polyglycol ether. It is available from Sigma-Aldrich, P.O. Box 14508, St. Louis, Mo. 63718 as well as the Dow Chemical Co., 2030 Dow Center, Midland, Mich. 48674. Other sources of TERGITOL™ will be apparent to those skilled in the art. Another option for a nonionic surfactant is SOFTANOL™ 70, available from Nippon Shokubai of Osaka 541-0043, Japan. Other branched or linear, primary or secondary, polyethoxylated alcohols can be used as nonionic surfactants.

Thus, Examples 1 and 2 include only nonionic surfactants. While these examples provide an excellent mechanism for delivering the active ingredient (e.g., TEG) and fragrance to odor-causing molecules residing in soft surfaces, it has been surprisingly found that the combination of nonionic and ionic surfactants provides still improved utility. Thus, small amounts of a quaternary ammonium salt in the form of Agent 2248-14 or BTC1010 are added in Examples 3 through 9. The combination of the quaternary ammonium salt with the nonionic surfactants provides improved penetration and delivery of the active ingredient deep into the problematic areas within carpeting, upholstery, bedding, drapes, etc.

By using a combination of nonionic and cationic surfactants, the disclosed compositions and methods provide a means for delivering TEG to odor-causing molecules buried deep within upholstery or carpeting. Thus, the TEG can be effectively delivered to deeply embedded odor-causing substances such as pet urine or other problematic odors. Further, Agent 2248-14, BTC1010, and other quaternary ammonium salts have anti-microbial properties and therefore add a sanitization function to the disclosed formulations. The total surfactant content preferably ranges from about 0.50 to about 2 wt %.

One preferred quaternary ammonium salt (Agent 2248-14) is a mixture of alkyl dimethyl benzyl ammonium chloride and alkyl dimethyl ethyl benzyl ammonium chloride. It is sold by the Stepan Company, 22 Frontage Road, Northfield, Ill. 60093 (www.stepan.com) in a preparation that is 25 wt % alkyl dimethyl benzyl ammonium chloride, 25 wt % alkyl dimethyl ethyl benzyl ammonium chloride, 2-3 wt % ethanol and the remainder water.

The most preferred quaternary ammonium salt is didecyl dimethyl ammonium chloride, also known as BTC 1010 or Quaternium 12.

A wide variety of cationic surfactants are available in addition to the quaternary ammonium salts discussed above. While quaternary ammonium salts are preferred, other cationic surfactants will be apparent to those skilled in the art without undue experimentation.

Aerosol formulations are provided in Examples 7 and 8, using nitrogen propellant and hydrocarbon propellant respectively.

Therefore, the disclosed method and compositions provide a new application for TEG, other glycols and other materials that are liquids at room temperature and that have a vapor pressure of less than 0.0035 mmHg at room temperature, as a malodor absorbent for soft surfaces. The use of TEG has been extended to treating odors embedded in soft surfaces such as carpeting and upholstery. When the composition is applied, a layer or an agglomeration is formed within the soft surface substrate in close proximity to the malodor sources. The odor-causing substance comes into contact with the agglomeration and is dissolve in the agglomeration thereby reducing its effective vapor pressure. Many malodorous substances, such as thiols, amines, acids, sulfites, etc., have a very low air/solvent partition coefficients (Henry's constant), which confirms the broad-spectrum odor suppression capability of TEG and other glycols. In summary, the malodorous substance preferably has a greater affinity for TEG than air thus reducing the vapor pressure and perception by the human sense of smell.

The agglomerations or droplets formed by the active ingredient (TEG, dipropylene glycol, propylene glycol, or material with a vapor pressure of less than 0.0035 mmHg at room temperature), carrier, fragrance and surfactants have an inner portion or core where the active ingredient, fragrance, and some carrier accumulate and an outer surface or outer portion where the surfactant has accumulated. The odor-causing substance is absorbed through the outer (surfactant) layer into the core of the agglomeration resulting in a reduction of the vapor pressure and therefore odor reduction.

The examples disclosed above are micro-emulsions of fragrance, TEG, ethanol and water. When applied, the microemulsion penetrates into the spaces between fibers of a soft surface. Upon evaporation, most of the volatile components (water and ethanol) are removed and a residual agglomeration or droplet of TEG, ethanol, water, fragrance and surfactant serves as an absorbent for odor-causing compounds and molecules. The agglomerations also serve as fragrance extenders.

One important characteristic of the disclosed composition is the abilities to penetrate rapidly and deeply into the soft surfaces for contacting the odor-causing substance. Methods to evaluate such abilities are provided herein. The disclosed methods make use of a Skein Test that measures the Surface Penetration Time (SPT) of the composition under different testing conditions. The equipments and procedures for conducting the Skein Test are discussed in detail below.

Apparatus

FIG. 1 graphically illustrates an anchoring assembly used in the Skein Test. The anchoring assembly includes a hook (A) of a standard weight connected to an anchor (C) through a thread (B). The anchoring assembly may be prepared by: 1) bending a piece of No. 10 B&S gage copper wire about $^{29}/_{16}$ in. (14.1 mm) long into the form of a hook as illustrated in FIG. 1; and 2) adjusting the weight of the bent hook to exactly 3.000 g. Nickel, silver, and stainless steel wire are even more suitable than copper for this purpose because they are more corrosion resistant.

The anchor (C) is a flat, cylindrical, lead slug with a minimum weight of 40 g and has a diameter of 1 in. (25 mm) and a thickness of about $^{3}/_{16}$ in. (4.7 mm). A loop of wire (D) is solder in the center of the anchor to serve as a small ring, or eye, for attaching the anchor to the hook with a fine linen thread (B) at a distance apart of 3/4 in. (19 mm). If many products are to be tested, prepare at least two hooks and anchors.

Test Skein

Skeins of various fabrics, such as cotton, silk, wool, and polyester, are suitable for use in the Skein Test to determine the Surface Penetration Time (SPT) of test compositions. It is noteworthy, however, that SPTs obtained using different types of skeins are not comparable to one another as the surface penetration abilities of the test compositions fabric-specific.

The most preferred skein is cotton skein, such as 40 s/2 combed Peeler yarn with a lisle twist of 18 to 20 turns in. and a balanced construction is suitable. Preferably, the yarn used for a given series of skein tests is from the same lot of cotton. The cotton skein may be purchased from Testfabrics, P. O. Drawe "O", Middlesex, N.J. 08846. The weights of the purchased cotton skeins need to be corrected individually to within 10 mg of 5 g or to within 1 grain of 77 grains.

For a Skein Test, fold a 5.00 g (77±1 grain) skein of yarn enough times to form a loop of 18 in. (460 mm) around. A 36 in. (910 mm) skein is most convenient and can be formed into an 18-in. loop with only two folds; a 54 in. (1370 mm) skein requires three folds; a 72 in. (1830 mm) skein, four folds; and a 90-in. (2290 mm) skein requires five folds.

Test Procedure

At room temperature, pour 500 mL test composition into a 500-mL graduated cylinder. Remove foam on the surface of the solution either with a 100-mL bulb pipet or with an aspirator. Fasten one end of the folded skein to the upper portion of the hook (A) and cut through the skein at the opposite end with shears. Draw the cut skein through the fingers when testing wetting agents in order to make it more compact. Fold into the skein near the hook any threads that have been tied around the skein to correct its weight.

Hold the skein in one hand with the anchor suspended in the test composition contained in the 500-mL graduated cylinder. Hold a stop watch in the other hand and release the skein. The anchor assembly immediately sinks towards the bottom of the graduated cylinder while simultaneously dragging the skein into the test composition. Start the stop watch when the anchor (C) makes contact with the bottom of the graduated cylinder.

Figure 2:
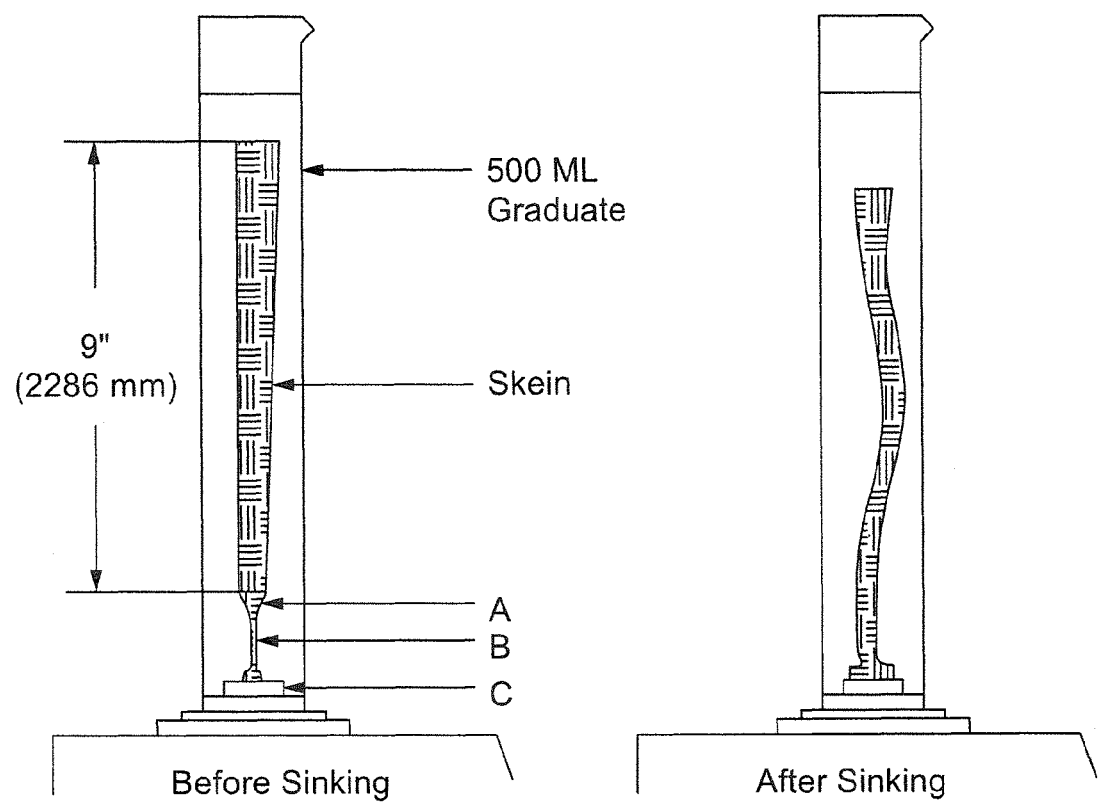
FIG. 2 graphically illustrates the Skein Test in accordance with this disclosure, particularly illustrating the position of the test skein before and after sinking.

The skein at first suspends or floats in the test composition due to its buoyancy thereby tensioning the thread (B) into a straight line and holding the hook (A) in a suspending position, as illustrated in FIG. 2 ("before sinking"). After the test composition completely penetrates through the skein and/or displaces the air trapped therein, the buoyancy of the skein becomes insufficient to keep the skein and hook (A) in a suspending or floating position. At this time, the skein and hook (A) starts to sink towards the bottom of the graduated cylinder thereby releasing the tension of the thread (B), as illustrated in FIG. 2 ("after sinking"). Stop the stop watch immediately after the skein or hook (A) starts to sink. The time recorded on the stop watch is the Surface Penetration Time of the test composition.

Obtain the average of at least four determinations of SPT for each composition tested. An average deviation of 10 to 12% among the determinations may be acceptable. Four comparison Skein Tests between the disclosed composition and a commercial composition using four different types of skeins are conducted. The results of the tests are listed in the table below.

TABLE 1

SPT Comparison Between a Disclosed Composition and An Existing Commercial Composition

| Skein Material | SPT (disclosed composition) | STP (existing commercial composition) |
|---|---|---|
| Cotton | 0 | 2.74 min |
| Polyester | 0 | 0 |
| Silk | 1.5 sec | 25 sec |
| Wool | 0 | 4.5 sec |

As clearly indicated in Table 1, the SPT of the disclosed composition is relatively short in silk skein test and close to zero, i.e. instant penetration, in cotton, silk and wool skein tests. The SPT of the commercial composition, on the other hand, is significantly longer than that of the disclosed composition in all skein tests except polyester, in which case the commercial composition also penetrate instantly through the polyester skein.

Thus, the disclosed composition exhibits significantly improved ability to penetrate rapidly and deeply into soft surfaces. As a result, the odor elimination performance of the disclosed composition is also improved over the existing odor elimination compositions because the odor-causing substance embedded deep into the soft surfaces, which cannot be effectively treated by the existing compositions and methods, can be reached and subsequently treated by the disclosed composition.

Without being bonded by any particular theory, the improved surface penetration may be a combinatorial result of factors such as the combination of surfactant, the active ingredient used, the selection of the solvent system, etc. In one embodiment, the disclosed composition has a Cotton Surface Penetration Time of no more than 2.5 minutes. In another embodiment, the disclosed composition has a Silk Surface Penetration Time of no more than 20 seconds. In yet another embodiment, the disclosed composition has a Wool Surface Penetration Time of no more than 4 seconds.

While only certain embodiments have been set forth, alternative embodiments and various modifications will be apparent from the above descriptions to those skilled in the art. These and other alternatives are considered equivalents and within the spirit and scope of this disclosure.

What is claimed:

1. A composition for treating odors embedded in or adsorbed onto soft surfaces, the composition comprising:
    at least one active ingredient selected from the group consisting of triethylene glycol, dipropylene glycol, propylene glycol, triethanolamine, and mixtures thereof, wherein the at least one active ingredient reduces the partial pressure of malodorants;

0.5-1.5 wt % nonionic surfactant comprising a mixture of a hydrogenated castor oil surfactant and a polyglycol ether;

0.1-1 wt % quaternary ammonium salt;

1-10 wt % co-solvent selected from the group consisting of short chain monohydric alcohol; and water, wherein the composition is free of any cyclodextrin compounds or film-forming polymers.

2. The composition of claim 1, wherein the active ingredient is present in the composition at a concentration of from 0.5 to 6.0 wt %.

3. The composition of claim 1, wherein the active ingredient is present in the composition at a concentration of from 0.5 to 1.5 wt %.

4. The composition of claim 1, wherein the total surfactant concentration of the composition is from 0.5 to 2.0 wt %.

5. The composition of claim 1, wherein the total surfactant concentration of the composition is from 1.0 to 2.0 wt %.

6. The composition of claim 1, wherein the polyglycol ether comprises an ethoxylation product of C11-C15 alkanol with ethylene oxide.

7. The composition of claim 1, wherein the quaternary ammonium salt comprises didecyldimethyl ammonium chloride.

8. The composition of claim 1, wherein the water content of the composition is from 75 to 95 wt %.

9. The composition of claim 1, further comprising a co-solvent selected from a group consisting of short-chain monohydric alcohols, glycol ethers, and mixtures thereof.

10. The composition of claim 9, wherein the co-solvent is present in the composition at a concentration of from 1 to 10 wt %.

11. The composition of claim 1, further comprising from 0.25 to 0.75 wt % fragrance.

12. A composition for treating odors embedded in or adsorbed onto soft surfaces, the composition comprising:

at least one active ingredient selected from the group consisting of triethylene glycol, dipropylene glycol, propylene glycol, triethanolamine, and mixtures thereof, wherein the at least one active ingredient reduces the partial pressure of malodorants;

0.5-1.5 wt % nonionic surfactant comprising a mixture of a hydrogenated castor oil surfactant and a polyglycol ether;

0.1-1 wt % quaternary ammonium salt;

1-10 wt % co-solvent selected from the group consisting of short chain monohydric alcohol; and 75-95 wt % water, wherein the composition is free of any cyclodextrin compounds or film-forming polymers.

13. The composition of claim 12, wherein the active ingredient is present in the composition at a concentration of from 0.5 to 1.5 wt %.

14. The composition of claim 12, wherein the total surfactant concentration of the composition is from 1.0 to 2.0 wt %.

15. A composition for treating odors embedded in or adsorbed onto soft surfaces, the composition comprising:

at least one active ingredient selected from the group consisting of triethylene glycol, dipropylene glycol, propylene glycol, triethanolamine, and mixtures thereof, wherein the at least one active ingredient reduces partial pressure of malodorants;

0.5-1.5 wt % nonionic surfactant comprising a mixture of a hydrogenated castor oil surfactant and a polyglycol ether;

0.1-1 wt % quaternary ammonium salt;

1-10 wt % co-solvent selected from a group consisting of short chain monohydric alcohol; and water, wherein the total surfactant concentration of the composition is from 0.5 to 2.0 wt %, and wherein the composition is free of any cyclodextrin compounds or film-forming polymers.

16. The composition of claim 15, wherein the active ingredient is present in the composition at a concentration of from 0.5 to 1.5 wt %.

* * * * *